(12) United States Patent
Liao et al.

(10) Patent No.: US 10,020,538 B2
(45) Date of Patent: Jul. 10, 2018

(54) SALTS FOR MULTIVALENT ION BATTERIES

(71) Applicant: UCHICAGO ARGONNE, LLC, Chicago, IL (US)

(72) Inventors: Chen Liao, Willowbrook, IL (US); Trevor L. Dzwiniel, Carol Stream, IL (US); Baofei Pan, Woodridge, IL (US); Sang-Don Han, Woodridge, IL (US); Anthony Burrell, Naperville, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 209 days.

(21) Appl. No.: 14/940,667

(22) Filed: Nov. 13, 2015

(65) Prior Publication Data

US 2017/0141432 A1    May 18, 2017

(51) Int. Cl.

| | | |
|---|---|---|
| *C01B 21/084* | (2006.01) | |
| *C01B 21/086* | (2006.01) | |
| *H01M 10/0563* | (2010.01) | |
| *H01M 10/0568* | (2010.01) | |
| *C07D 233/90* | (2006.01) | |

(52) U.S. Cl.
CPC ....... *H01M 10/0568* (2013.01); *C01B 21/084* (2013.01); *C01B 21/086* (2013.01); *C07D 233/90* (2013.01); *H01M 10/0563* (2013.01)

(58) Field of Classification Search
None
See application file for complete search history.

(56) References Cited

U.S. PATENT DOCUMENTS

| | | |
|---|---|---|
| 8,377,406 B1 | 2/2013 | Singh et al. |
| 8,722,005 B1 | 5/2014 | Poshusta et al. |
| 2011/0311884 A1 | 12/2011 | Armand et al. |
| 2012/0041233 A1 | 2/2012 | Sato et al. |
| 2014/0075746 A1 | 3/2014 | Schmidt |
| 2014/0142338 A1 | 5/2014 | Johnson |
| 2014/0241973 A1 | 8/2014 | Fukunaga et al. |
| 2016/0016797 A1* | 1/2016 | Maekawa ............. C07C 303/40 423/386 |
| 2016/0308247 A1* | 10/2016 | Buisine ............... C01B 21/0935 |
| 2017/0047607 A1* | 2/2017 | Schmidt ............... C01B 21/086 |

OTHER PUBLICATIONS

Niedzicki, L. et al., New Type of Imidazole Based Salts Designed Specifically for Lithium Ion Batteries, Electrochimica Acta 55, 1450-1454 (2010).
Singh, S. et al., Bis(fluorosulphuryl)imide Derivatives of Zinc (II), Cadmium (II), Mercury (II) and Their Coordination Complexes With Oxygen and Nitrogen Donors, Indian Journal of Chemistry, vol. 28A, 890-892 (1989).

* cited by examiner

*Primary Examiner* — Wayne Langel
(74) *Attorney, Agent, or Firm* — Olson & Cepuritis, Ltd.

(57) ABSTRACT

Methods for preparing electrolyte salts for alkaline earth metal-ion batteries (e.g., calcium and magnesium ion batteries) are described. The electrolyte salts comprise alkaline earth metal (e.g., Mg or Ca) salts of bis(fluorosulfonyl)imide (FSI) and 3,4-dicyano-2-trifluoromethylimidazole (TDI). The methods comprise contacting FSI or TDI with an alkaline earth metal bis(trifluoroacetate) salt in trifluoroacetic acid.

10 Claims, 4 Drawing Sheets

(A)

(B)

(C)

(D)

SALTS FOR MULTIVALENT ION BATTERIES

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to materials for use in electrolytes of energy storage devices, notably non-aqueous electrochemical cells and batteries, and more particularly, to salts for use in electrolytes for non-aqueous multivalent electrochemical cells and batteries, and methods for preparing the salts.

BACKGROUND

Rechargeable lithium ion batteries are increasingly used for a variety of energy storage applications, including for example, electric and hybrid automotive applications throughout the world. In automotive applications, particularly for all-electric vehicles, battery weight is a major hurdle for achieving longer driving range-per charge. While, lithium ion (Li-ion) batteries remain a very important commercial and research focus, there is an increasing need for new battery technologies to provide higher energy densities than are available for Li-ion.

One promising approach to higher-energy density alternative to Li-ion batteries is a battery based on a multivalent ion electrolyte, such as magnesium (Mg) or calcium (Ca). Li-ion, with a charge of +1, can provide only a single electron for an electrical current, whereas multivalent ions (e.g., with a charge of +2 or +3) have the potential to provide two or more the electrical current of Li-ions (depending on the charge of the multivalent ion) if present with the same density. Mg-ion and Ca-ion batteries have promise, however, there are also a number of issues that still need to be worked out and better understood. Calcium ion and magnesium ion provide relatively high potentials ($Ca^{2+}$: −2.87 relative to standard hydrogen electrode, SHE; $Mg^{2+}$: −2.37 vs. SHE) suitable for many secondary battery requirements. One of the most relevant aspects is understanding the mechanism of reversible plating and stripping of Mg at the metal anode/electrolyte interface during battery operation. So far, reversible Mg plating has been achieved with only a narrow class of electrolytes, inorganic or organic magnesium aluminum chloride salts dissolved in ethereal solutions. For example, the Mg analogues to the most common commercial Li-ion electrolytes instantaneously decompose and passivate the Mg metal anode surface preventing further electrochemical reaction, consequently blocking the battery.

There are ongoing needs for new electrolyte salts for multivalent ion batteries, particularly Mg-ion and Ca-ion batteries, and for improved methods of preparing such salts. The salts and methods described herein address these needs.

SUMMARY OF THE INVENTION

Methods for preparing electrolyte salts for alkaline earth metal-ion batteries (e.g., calcium and magnesium ion batteries) are described. The electrolyte salts comprise alkaline earth metal (e.g., Mg or Ca) salts of bis(fluorosulfonyl)imide (FSI) and 3,4-dicyano-2-trifluoromethylimidazole (TDI). The methods comprise contacting FSI or TDI with an alkaline earth metal bis(trifluoroacetate) salt in trifluoroacetic acid. In a typical reaction, at least about 0.5 molar equivalents (i.e., equivalents based on moles of alkaline earth metal ion compared to moles of FSI or TDI) of the alkaline earth metal bis(trifluoroacetate) salt is dissolved in trifluoroacetic acid (e.g., at a molar concentration of about 0.05 to about 2 molar). Generally, the FSI or TDI is contacted with about 0.45 to about 0.75 molar equivalents of the alkaline earth metal bis(trifluoroacetate) salt. Typically, the reactions are performed at temperatures in the range of about 10 to about 80° C. (generally about 15 to about 25° C.) for about 0.5 to about 8 hours. In some embodiments, the step of recovering the FSI or TDI salt comprises either filtration to recover the desired salt, or evaporation of the solvent to recover the salt as a solid (e.g., a powder).

While alkaline earth metal salts of TDI and FSI can be prepared by reaction of TDI and FSI with an alkaline earth metal hydroxide, such reactions often lead to impurities and degradation of the FSI and TDI. The methods for preparing TSI and TDI alkaline earth metal salts described herein, utilizing alkaline earth metal bis(trifluoroacetate) salts in trifluoroacetic acid are mild and provide the corresponding $M(FSI)_2$ salts in surprisingly good yields and purity compared to the reactions with the metal hydroxides.

BRIEF DESCRIPTION OF THE DRAWINGS

The invention consists of certain novel features and a combination of parts hereinafter fully described, illustrated in the accompanying drawings, it being understood that various changes in the details may be made without departing from the spirit, or sacrificing any of the advantages of the present invention.

DETAILED DESCRIPTION OF PREFERRED EMBODIMENTS

Figure 1:
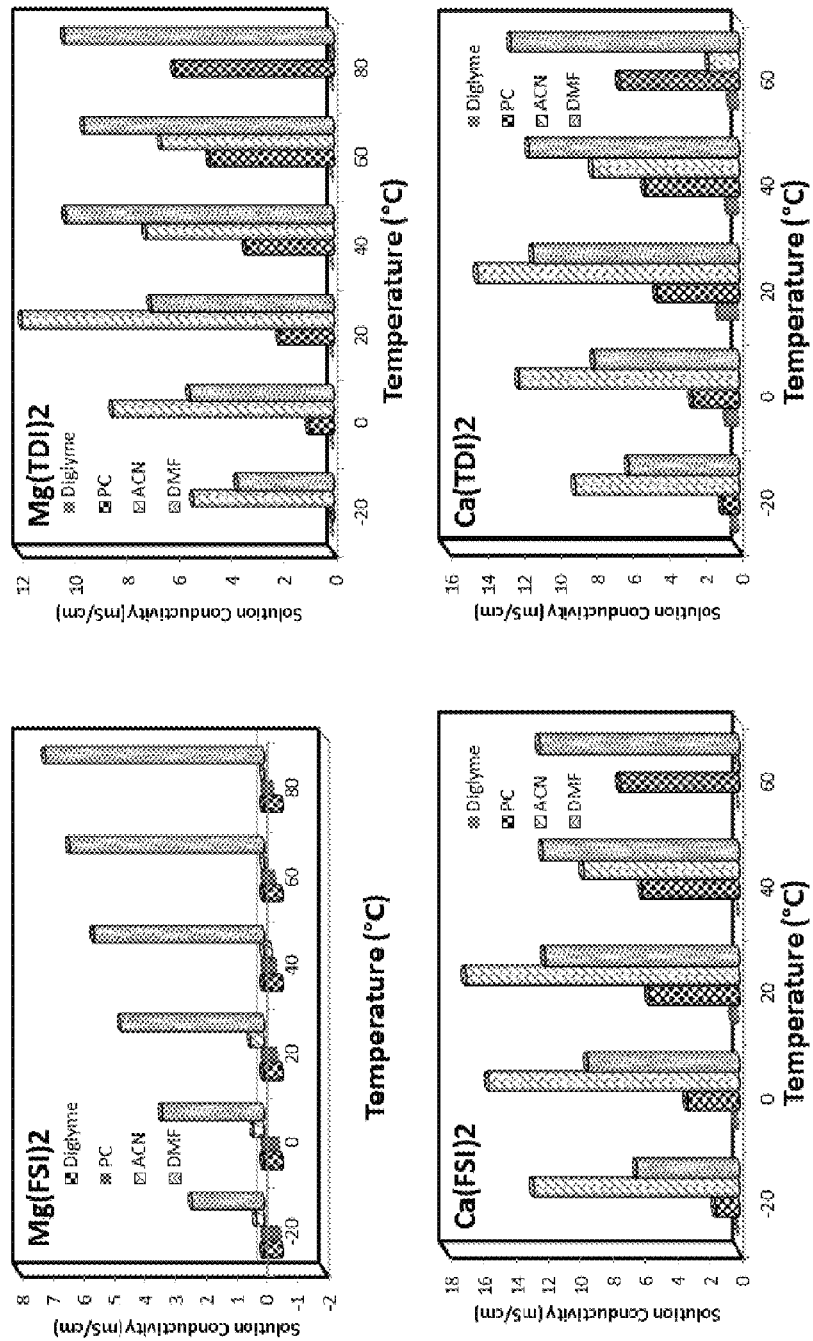
FIG. 1 illustrates conductivity profiles over the temperature range of −20 to +80° C. for (a) $Mg(TDI)_2$, (b) $Mg(FSI)_2$, (c) $Ca(TDI)_2$ and (d) $Ca(FSI)_2$.

The present invention provides, methods for preparing electrolyte salts for alkaline earth metal-ion batteries (e.g., calcium and magnesium ion batteries).

In one embodiment, the electrolyte salts comprises an alkaline earth metal (e.g., Mg or Ca) salt of bis(fluorosulfonyl)imide (FSI), and the method comprises contacting FSI with an alkaline earth metal bis(trifluoroacetate) salt of formula $(CF_3CO_2)_2M$, M=an alkaline earth metal such as Mg or Ca, dissolved in in trifluoroacetic acid:

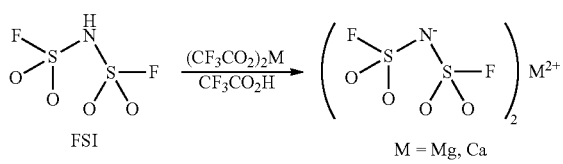

and then recovering the resulting M(FSI)$_2$ salt.

In another embodiment, the electrolyte salts comprises an alkaline earth metal (e.g., Mg or Ca) salt of 3,4-dicyano-2-trifluoromethylimidazole (TDI), and the method comprises contacting TDI with an alkaline earth metal bis(trifluoroacetate) salt of formula (CF$_3$CO$_2$)$_2$M, M=Mg or Ca, dissolved in in trifluoroacetic acid:

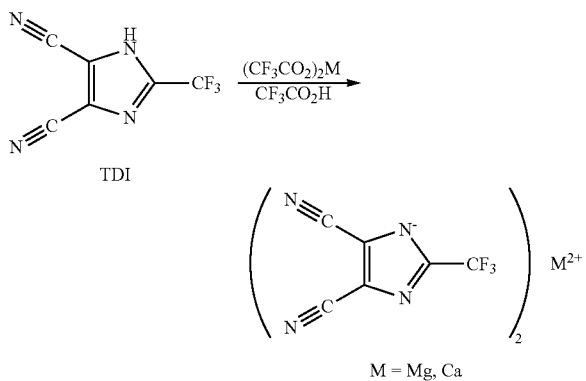

and then recovering the resulting M(TDI)$_2$ salt.

In a typical reaction, at least about 0.5 molar equivalents of the alkaline earth metal bis(trifluoroacetate) salt, (CF$_3$CO$_2$)$_2$M (i.e., equivalents based on moles of alkaline earth metal ion compared to moles of FSI or TDI) is dissolved in trifluoroacetic acid, e.g., at a molar concentration of about 0.05 to about 2 molar, or more typically about 0.4 to about 0.8 molar.

The reaction to form the salt can be performed at any temperature below the boiling point of trifluoroacetic acid. Typically, the reactions are performed at temperatures in the range of about 10 to about 80° C. (generally about 15 to about 25° C.) for about 0.5 to about 8 hours.

The (CF$_3$CO$_2$)$_2$M salts can be prepared in any convenient manner. Typically, the (CF$_3$CO$_2$)$_2$M salts are prepared by reaction of the corresponding alkaline earth metal hydroxide with excess trifluoroacetic acid.

TDI and FSI are known materials, which can be purchased commercially or prepared by any of a number of methods, including, but not limited to the methods described in the Examples set forth herein.

The M(FSI)$_2$ and M(TDI)$_2$ salts typically are recovered by either filtration or evaporation of the solvent. The FSI and TDI salts also can be purified, if desired, e.g., by crystallization following techniques that are well known in the chemical arts.

The M(FSI)$_2$ and M(TDI)$_2$ salts described herein can be utilized in a non-aqueous electrolyte for an alkaline earth metal ion battery. Such electrolytes typically comprise the salt dissolved in a non-aqueous solvent, which can include a single solvent or a combination of two or more solvents. Non-limiting examples of such solvents include ethylene carbonate, propylene carbonate, dimethyl carbonate, and ethyl methyl carbonate, as well as combinations of two or more such carbonates. Non-limiting examples of other non-aqueous solvents include esters (e.g., gamma-butyrolactone, methyl formate, methyl acetate), ethers (e.g., diethoxyethane, dimethoxyethane (also known as glyme), bis(2-methoxyethyl) ether (also known as diglyme), tetrahydrofuran, 2-methyltetrahydrofuran, 1,3-dioxane), nitriles (e.g., acetonitrile), sulfolanes, and the like. The non-aqueous solvent preferably comprises an organic carbonate, such as dimethyl carbonate (DMC), ethyl methyl carbonate (EMC), ethylene carbonate (EC), propylene carbonate (PC), or a combination of two or more of the foregoing. A preferred solvent comprises ethylene carbonate and ethyl methyl carbonate in respective weight ratio of approximately 3:7. Preferably, the concentration of lithium salt in the non-aqueous solvent is in the range of about 0.1 molar (M) to about 5 molar, more preferably about 1 M to about 1.5 M (e.g., about 1.2 M), for example, 1.2 M LiPF$_6$ in ethylene carbonate/ethyl methyl carbonate (3:7 weight ratio).

EXAMPLE 1

Preparation of TDI

A glass reactor (2 L, jacketed) equipped with an internal temperature probe, mechanical stirrer, and gas inlet/outlet adapters was flushed with nitrogen. The jacket of the reactor was connected to a Huber UNISTAT 405 heating/chilling circulator. The reactor was charged with diaminomaleonitrile (400 g,) and THF (1600 mL) and the temperate controller was set to 0° C. Trifluoroacetic anhydride (940 g) was added to the cooled solution of diaminomaleonitrile by peristaltic pump over a period of about 2.5 hours (rate set at 150-200 mL/h). Once the addition was complete, the mixture was warmed from 0° C. to 20° C. over a period of about 1 hour, at which time, an HPLC showed complete consumption of the diaminomaleonitrile to form a trifluoroacetamide intermediate.

After all diaminomaleonitrile was depleted, the reaction mixture was heated to 73° C. to effect cyclization of the trifluoroacetamide intermediate to form 3,4-dicyano-2-trifluoromethylimidazole. After about 4 hours of heating, the HPLC showed complete conversion to 3,4-dicyano-2-trifluoromethylimidazole. The mixture was cooled and kept stirring at 20° C. overnight. The cooled mixture was transferred to a ROTOVAP rotary evaporator and the volatiles were removed by evaporation to a thick dark oil. Portions of water (50 mL) were added and evaporated in the same manner until any remaining trifluoroacetic acid was substantially gone.

The dark semi-solid mixture was dissolved in ethanol (1300 mL) and transferred back to the 2 L reactor. Lithium carbonate (160.62 g) was added in portions, and the reaction mixture was stirred for about 40 minutes and then was filtered through a CELITE pad. The filtrate was returned to the 2 L reactor and stirred with activated carbon (about 122 g) overnight, followed by heating at 45° C. for about two hours. The carbon was removed by filtration while the solution was still warm. The filtrate was evaporated under vacuum (by rotary evaporation) to an orange/tan solid. This solid was slurried in methyl-t-butyl ether (MTBE; about 1300 mL) with overhead stirring to break up the larger chunks. The solids were filtered and air-dried overnight. The off-white solid filter cake (about 712 g) was dissolved in 2-methyltetrahydrofuran (about 2 L) and filtered. MTBE (about 2 L) was added to the filtrate to precipitate the product (3,4-dicyano-2-trifluoromethylimidazole; TDI). A second crop was obtained after concentration of the mother liquor and addition of more MTBE. The two crops (about 243 g and about 273 g) were combined and dissolved in warm (40° C.) acetonitrile (about 2 L). The resulting slightly cloudy solution was filtered to clarify. After cooling and concentrating on the rotary evaporator, two crops were obtained (about 176 g and about 107 g). The solids were dried at about 70° C. for about 24 hours, then at about 110° C. for about 24 hours. HPLC>99.9%. $^{13}$C NMR (125 MHZ; DMSO-$d_6$)/ppm: 147.8 (q, J=36.5 Hz), 120.6 (q, J=267 Hz), 119.3 (s), 115.5 (s). $^{19}$F NMR (470 MHZ; DMSO-$d_6$)/ppm: −62.4. FT IR/cm$^{-1}$: 2250 (CN stretch).

EXAMPLE 2

Preparation of FSI

A. Preparation of Bis(chlorosulfonyl)imide:

A 2 L three-neck flask was charged with sulfamic acid (about 225 g), and suspended in thionyl chloride (about 465 mL), all under a nitrogen atmosphere. Chlorosulfonic acid (about 153 mL) was added and the heterogeneous mixture was heated with a temperature-controlled heating mantle in stages to about 130° C. and then held at that temperature overnight. All gases emitted from the reaction (via nitrogen purge) were trapped in a 2 molar NaOH solution. After heating, the reaction mixture was slightly yellow in color, but clear. The reaction mixture was then fractionally distilled under vacuum at about 115-117° C. and about 7 Torr. A very pale yellow liquid (about 449 g) was collected, which solidified on standing. FTIR matched the literature reports for bis(chlorosulfonyl)imide.

B. Conversion of Bis(chlorosulfonyl)imide to FSI:

Bis(chlorosulfonyl)imide (about 120.06 g) was melted and transferred to a three neck 500 mL round bottom flask. The flask was kept at about 40° C. and BiF$_3$ (about 100.25 g) was added in portions, keeping the temperature between about 40° C. and 50° C., with brief cooling in a water bath. The mixture was then stirred overnight at room temperature. Bis(fluorosulfonyl)imide (FSI) was distilled directly from the reaction mixture at about 6 Torr and 50-80° C. The distillate (about 93 g) was collected and fractionally distilled, with a center cut of boiling range of about 50-51° C. at about 5.8 Torr.

EXAMPLE 3

Preparation of Mg(FSI)$_2$ Salt

Magnesium hydroxide (0.3685 g) was added in portions to stirring trifluoroacetic acid (6.4 g) in a reaction tube. The mixture warmed considerably during addition. After the addition, the mixture was heated briefly to boiling and an additional 2 mL of TFA was added to obtain a clear solution. Upon cooling, this generated a faint suspension. A solution of FSI (2.2878 g) in TFA (7.6163 g) was added to the mixture. Little change was noticed in the reaction mixture. The mixture was heated again to boiling without noticeable change. After cooling and stirring 2 hours, the solvent was evaporated under a nitrogen flow to obtain an oil. Drying under high vacuum at 60° C. formed a slightly off-white powder (1.37 g). FTIR matches the expected structure, without noticeable Mg(TFA)$_2$.

EXAMPLE 4

Preparation of Ca(FSI)$_2$ Salt

Calcium hydroxide (0.4097 g) was added in portions to stirring trifluoroacetic acid (10 mL) in a reaction tube. The mixture warmed considerably during addition. After the addition, the mixture was heated briefly to boiling to obtain a clear solution. Upon cooling, this generated a faint suspension. FSI (2.0861 g) was added to the mixture, forming a thicker suspension. The mixture was heated again to boiling without noticeable change. After cooling and stirring 2 hours, an oil layer separated. Upon slight cooling, this oil solidified. The solids were stirred overnight, then filtered under nitrogen and washed with dichloromethane (DCM; 3×3 mL). The white solids were transferred to a dry box and dried at 70° C. overnight to provide 1.80 g of Ca(FSI)$_2$ salt. FTIR matches the expected structure, without noticeable Ca(TFA)$_2$.

EXAMPLE 5

Preparation of Mg(TDI)$_2$ Salt

Magnesium hydroxide (about 0.37 g) is added in portions to stirring trifluoroacetic acid (6.4 g) in a reaction tube. The mixture will warm considerably during addition. After the addition, the mixture is heated briefly to boiling and an additional 2 mL of TFA is added to obtain a clear solution. Upon cooling, a solution of about 2 molar equivalents of TDI (based on equivalents of magnesium) In TFA is added to the mixture. After further cooling and stirring for about 2 hours, the solvent is evaporated under a nitrogen flow to obtain an oil, which upon drying under high vacuum at provides the solid Mg(TDI)$_2$ Salt.

EXAMPLE 6

Preparation of Ca(TDI)$_2$ Salt

Calcium hydroxide (about 0.41 g) is added in portions to stirring trifluoroacetic acid (10 mL) in a reaction tube. The mixture will warm considerably during addition. After the addition, the mixture is heated briefly to boiling. Upon cooling, a solution of about 2 molar equivalents of TDI (based on equivalents of calcium) in TFA is added to the mixture. After further cooling and stirring for about 2 hours, the solvent is evaporated under a nitrogen flow to obtain an oil, which upon drying under high vacuum at provides the solid Ca(TDI)$_2$ Salt.

EXAMPLE 7

Alternate Preparation of Alkaline Earth Metal FSI Salts

FSI is dissolved in a solution of about 0.5 molar equivalents of an alkaline earth metal bis(trifluoroacetate) salt of formula (CF$_3$CO$_2$)$_2$M in trifluoroacetic acid (i.e., equivalents based on moles of alkaline earth metal ion compared to moles of FSI), where M is an alkaline earth metal (e.g., Mg or Ca). The concentration of (CF$_3$CO$_2$)$_2$M in the trifluoroacetic acid solution is about 0.05 to about 2 molar. The mixture is maintained at a temperature below the boiling point of trifluoroacetic acid, e.g., at a temperature in the range of about 10 to about 80° C. for about 0.5 to about 8 hours. The alkaline earth metal salt of FSI (M(FSI)$_2$) is then recovered by either filtration or evaporation of the trifluoroacetic acid solvent. The (CF$_3$CO$_2$)$_2$M salt is prepared by addition of a alkaline earth metal hydroxide to trifluoroacetic acid.

EXAMPLE 8

Alternate Preparation of Alkaline Earth Metal TDI Salts

TDI is dissolved in a solution of about 0.5 molar equivalents of an alkaline earth metal bis(trifluoroacetate) salt of formula $(CF_3CO_2)_2M$ in trifluoroacetic acid (i.e., equivalents based on moles of alkaline earth metal ion compared to moles of TDI), where M is an alkaline earth metal (e.g., Mg or Ca). The concentration of $(CF_3CO_2)_2M$ in the trifluoroacetic acid solution is about 0.05 to about 2 molar. The mixture is maintained at a temperature below the boiling point of trifluoroacetic acid, e.g., at a temperature in the range of about 10 to about 80° C. for about 0.5 to about 8 hours. The alkaline earth metal salt of TDI $(M(TDI)_2)$ is then recovered by either filtration or evaporation of the trifluoroacetic acid solvent. The $(CF_3CO_2)_2M$ salt is prepared by addition of a alkaline earth metal hydroxide to trifluoroacetic acid.

EXAMPLE 9

Physicochemical Evaluation of $M(FSI)_2$ and $M(TDI)_2$ Salts

The conductivity of solutions of $Mg(FSI)_2$, $Ca(FSI)_2$, $Mg(TDI)_2$ and $Ca(TDI)_2$ were evaluated is several different non-aqueous solvents: diglyme, propylene carbonate (PC), dimethylformamide (DMF), and acetonitrile (ACN). Conductivity profiles over the temperature range of −20 to +80° C. are provided in FIG. 1. As is evident from the graphs in FIG. 1, the all of the salts provided relatively high conductivities in DMF, with conductivity increasing steadily with increasing temperature, whereas none of the salts exhibited significant conductivity in diglyme. $Ca(FSI)_2$, $Mg(TDI)_2$ and $Ca(TDI)_2$ each provided an intermediate level of conductivity in PC, whereas $Mg(FSI)_2$ had very low conductivity in PC.

Figure 2:
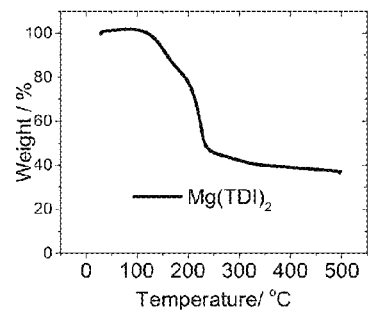
FIG. 2 provides thermogravimetric analysis (TGA) curves for (A) $Mg(TDI)_2$, (B) $Mg(FSI)_2$, (C) $Ca(TDI)_2$ and (D) $Ca(FSI)_2$.
Figure 2:
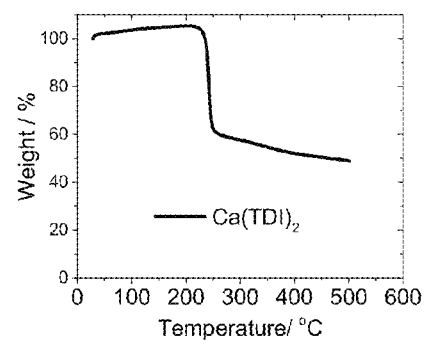
Figure 2:
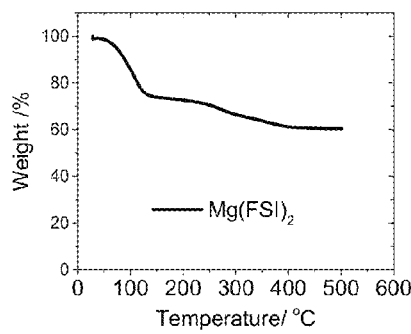
Figure 2:
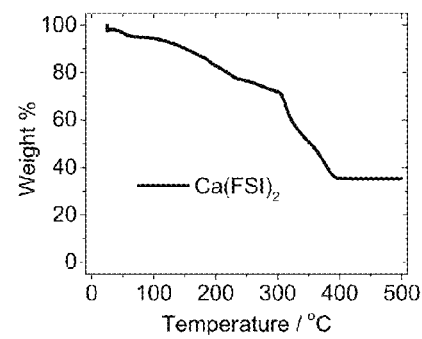
Figure 3:
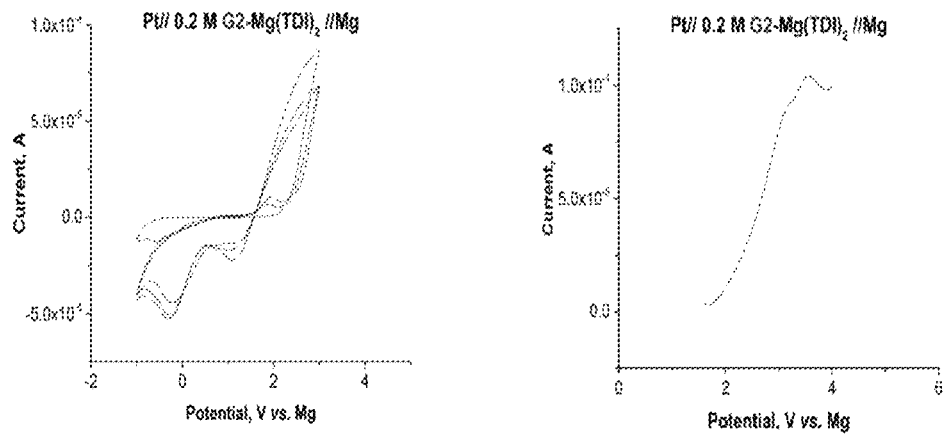
FIG. 3 provides (left) cyclic voltametry and (right) linear sweep voltametry curves for $Mg(TDI)_2$ vs. Mg metal FIG. 4 provides (left) cyclic voltametry and (right) linear sweep voltametry curves for $Ca(TDI)_2$ vs. Ca metal.
Figure 4:
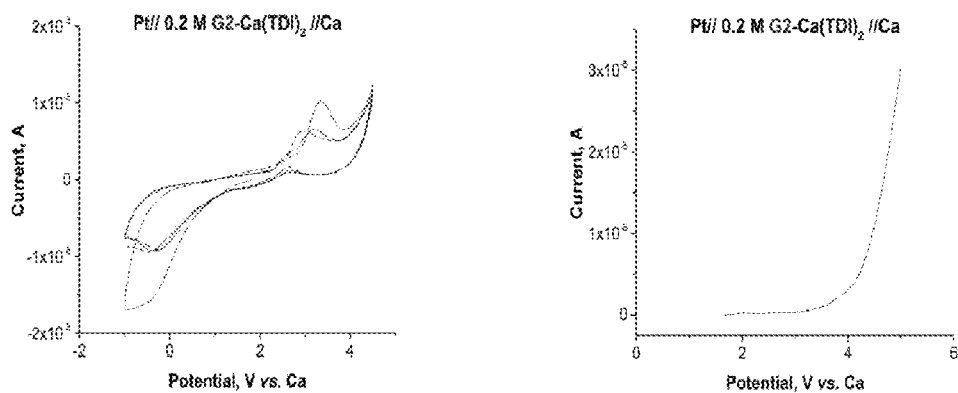
Figure 5:
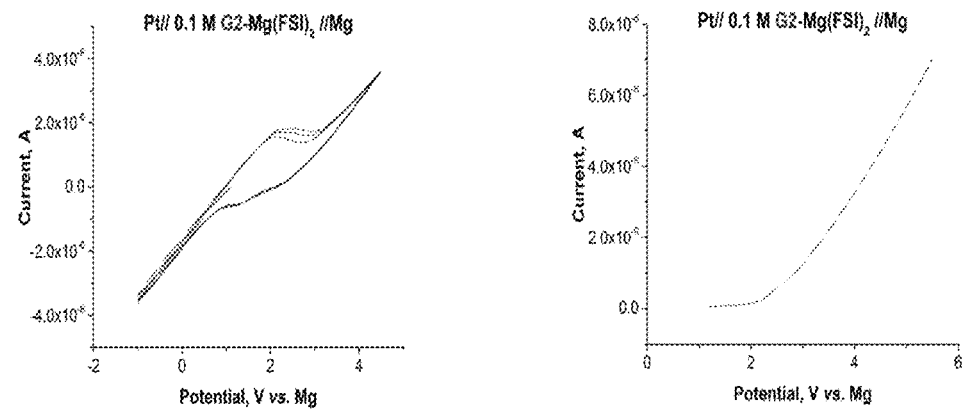
FIG. 5 provides (left) cyclic voltametry and (right) linear sweep voltametry curves for $Mg(FSI)_2$ vs. Mg metal.
Figure 6:
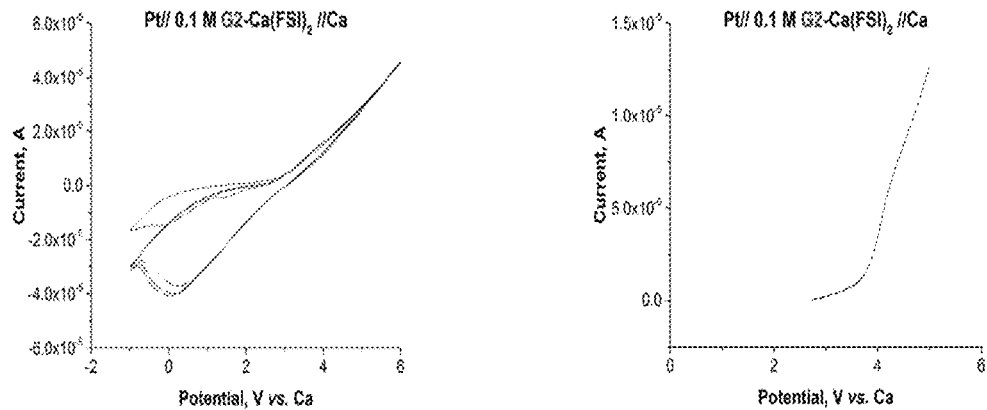
FIG. 6 provides (left) cyclic voltametry and (right) linear sweep voltametry curves for $Ca(FSI)_2$ vs. Ca metal.

Thermal stability of the salts were evaluated by thermogravimetric analysis (TGA). the TGA curves for $Mg(TDI)_2$, $Ca(TDI)_2$, $Mg(FSI)_2$, and $Ca(FSI)_2$, are provided in FIG. 2, Panels A, B, C and D, respectively. The calcium salts tended to remain stable over a greater temperature range than the corresponding magnesium salts.

In addition, the electrochemical stability of the salts was evaluated by cyclic voltametry and linear sweep voltametry. The electrochemical results are shown in FIGS. 3, 4, 5 and 6 for $Mg(TDI)_2$, $Ca(TDI)_2$, $Mg(FSI)_2$, and $Ca(FSI)_2$, respectively. $Ca(TDI)_2$ and $Ca(FSI)_2$ both were stable up to +4.0V vs. metallic Ca.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The terms "consisting of" and "consists of" are to be construed as closed terms, which limit any compositions or methods to the specified components or steps, respectively, that are listed in a given claim or portion of the specification. In addition, and because of its open nature, the term "comprising" broadly encompasses compositions and methods that "consist essentially of" or "consist of" specified components or steps, in addition to compositions and methods that include other components or steps beyond those listed in the given claim or portion of the specification. Recitation of ranges of values herein are merely intended to serve as a shorthand method of referring individually to each separate value falling within the range, unless otherwise indicated herein, and each separate value is incorporated into the specification as if it were individually recited herein. All numerical values obtained by measurement (e.g., weight, concentration, physical dimensions, removal rates, flow rates, and the like) are not to be construed as absolutely precise numbers, and should be considered to encompass values within the known limits of the measurement techniques commonly used in the art, regardless of whether or not the term "about" is explicitly stated. All methods described herein can be performed in any suitable order unless otherwise indicated herein or otherwise clearly contradicted by context. The use of any and all examples, or exemplary language (e.g., "such as") provided herein, is intended merely to better illuminate certain aspects of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The embodiments of the invention in which an exclusive property or privilege is claimed are defined as follows:

1. A method for preparing an alkaline earth metal salt of bis(fluorosulfonyl)imide (FSI) useful as an electrolyte salt for an alkaline earth metal-ion battery, the method comprising:

contacting FSI with a solution containing at least 0.5 molar equivalents of an alkaline earth metal bis-trifluoroacetate salt of the formula $(CF_3CO_2)_2M$, dissolved in trifluoroacetic acid to form an FSI salt of formula:

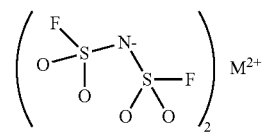

wherein M is an alkaline earth metal; and
recovering the FSI salt.

2. The method of claim 1, wherein M is Mg.

3. The method of claim 1, wherein M is Ca.

4. The method of claim 1, wherein FSI is contacted with about 0.45 to about 0.75 molar equivalents of the salt of the formula $(CF_3CO_2)_2M$.

5. The method of claim 4, wherein M is Mg.

6. The method of claim 4, wherein M is Ca.

7. The method of claim 1, wherein salt of the formula $(CF_3CO_2)_2M$, is dissolved in trifluoroacetic acid at a concentration in the range of about 0.05 to about 2 molar.

8. The method of claim 7, wherein M is Mg.

9. The method of claim 7, wherein M is Ca.

10. The method of claim 1, wherein the step of recovering the FSI salt comprises filtration or evaporation of trifluoroacetic acid solvent.

* * * * *